(12) United States Patent
Barton et al.

(10) Patent No.: US 7,456,961 B2
(45) Date of Patent: Nov. 25, 2008

(54) APPARATUS AND METHOD FOR DETECTING AEROSOL

(75) Inventors: Steven M. Barton, Everett, WA (US); Larry G. Trotter, Auburn, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/106,140

(22) Filed: Apr. 14, 2005

(65) Prior Publication Data

US 2006/0232773 A1    Oct. 19, 2006

(51) Int. Cl.
*G01N 21/00* (2006.01)
(52) U.S. Cl. .................................. 356/338; 356/337
(58) Field of Classification Search ............... 340/630, 340/628; 250/574; 356/338
See application file for complete search history.

(56) References Cited

U.S. PATENT DOCUMENTS

| | | | | |
|---|---|---|---|---|
| 5,644,388 A | * | 7/1997 | Maekawa et al. | 356/73 |
| 5,678,126 A | * | 10/1997 | Rathbun | 399/30 |
| 6,377,183 B1 | | 4/2002 | Baker et al. | |
| 2004/0246479 A1 | * | 12/2004 | Cartlidge et al. | 356/335 |
| 2005/0002021 A1 | * | 1/2005 | Kreh et al. | 356/237.2 |
| 2006/0202847 A1 | * | 9/2006 | Oppelt et al. | 340/630 |

OTHER PUBLICATIONS

Thorsten Schultze, Ingolf Willms, Smoke And Dust Monitoring By A Microscope Video Sensor, *AUBE '04, International Conference On Automatic Fire Detection*, Sep. 14-16, 2004, 7 pages, University Duisburg-Essen, Duisburg, Germany.

* cited by examiner

*Primary Examiner*—Gregory J Toatley, Jr.
*Assistant Examiner*—Tri T Ton
(74) *Attorney, Agent, or Firm*—Alston & Bird LLP

(57) ABSTRACT

The apparatus and method for detecting aerosol includes transmitting a light beam, focusing at least one image sensor having a field of view that encompasses at least a portion of the light beam on a portion of the light beam, capturing an image of the light beam by the image sensor(s), and detecting aerosol if the image of the light beam has a predefined shape and at least a predetermined intensity. Therefore, the apparatus and method for detecting aerosol permit the accurate detection of aerosol, while ignoring the stray contaminants that routinely cause false alarms in conventional aerosol detectors. In particular, an image of a light beam is sensed when aerosol is present, such that random contaminants that adhere to the walls of a detection chamber or that pass through the light beam do not affect the aerosol detection.

25 Claims, 3 Drawing Sheets

NO AEROSOL

AEROSOL

APPARATUS AND METHOD FOR DETECTING AEROSOL

FIELD OF THE INVENTION

The apparatus and method of the present invention provide aerosol detection by detecting a light beam when the aerosol is present about the light beam. In particular, the apparatus and method of the present invention provide for the detection of a predefined shape and a predetermined intensity of the light beam when aerosol is present.

BACKGROUND OF THE INVENTION

Aerosol detectors are commonly used to detect the presence of aerosol particles, such as smoke, fog and/or dust particles, in the air. The most commonly used type of aerosol detector measures light that is scattered from a light beam onto a photo sensor by aerosol particles that come into contact with the light beam. This type of aerosol detector typically includes a housing that defines a chamber that allows smoke or other aerosols to enter without allowing light to enter from the outside. A light source, such as a light emitting diode (LED), is disposed within the chamber for emitting light. A detector or photo sensor, such as a photoelectric eye or photodiode, is also disposed within the chamber. In the absence of aerosol, most of the light emitted by the light source is typically absorbed by the chamber walls or some other light trap prior to reaching the detector. In this regard, the walls of the chamber are typically constructed of or treated with a non-reflecting material to minimize the light incident upon the photo sensor due to reasons other than the scattering from the light beam by aerosol particles that come into contact with the light beam. For example, the walls of the chamber may be painted a dark color, such as flat black, in order to absorb most of the light incident thereupon. If aerosol is present within the chamber, however, the light is scattered by the aerosol particles, and a portion of the scattered light is received by the detector, which can cause an alarm if the incident light exceeds a predetermined limit that is indicative of an undesirable concentration of aerosol.

Unfortunately, the conventional aerosol detector design permits a significant number of false alarms. Because conventional aerosol detectors measure the light scattered within a detection chamber, these aerosol detectors will issue an alarm anytime the photo sensor measures scattered light regardless of whether the scattered light is due to the presence of aerosol or some other contaminant. As a result, the presence of condensation, dust, fibers and insects reflects and/or scatters light, which frequently causes false alarms. For example, in certain environments, such as the cargo areas of aircraft, in which aerosol detectors are used to sense smoke, a significant amount of dirt, dust, fibers and other small particles are in the air. It is estimated that the ratio of false smoke alarms in some commercial aircraft cargo compartments to real smoke alarms is as high as 200:1. The random particles may enter the detection chamber and while the amount of light scattered by the particles may not be enough to cause an alarm initially, the particles may land on the walls of the chamber and, over time, cause enough reflection off of the chamber walls to activate a false alarm. In addition, contaminants passing through the light beam, such as insects also may cause enough reflection and/or scattering to activate a false alarm.

False alarms may be very costly. For example, a false smoke alarm in an operating aircraft may cause diversion of the aircraft, which inconveniences passengers, disrupts one or more aircraft schedules, and necessitates unscheduled maintenance on the aircraft, all of which impose significant costs on the operator of the aircraft. In other applications, such as in public buildings and homes, false alarms lead to the evacuation of the structure, automatic response by emergency personnel and damage caused by unnecessary release of automatic fire extinguishing systems, which are costly disruptions.

Thus, there is a need for an aerosol detector that is capable of accurately identifying the presence of aerosol within the detector and also capable of greatly reducing the likelihood of false alarms due to stray contaminants that may enter the detector.

BRIEF SUMMARY OF THE INVENTION

The apparatus and method for detecting aerosol of the present invention permit the accurate detection of aerosol, while ignoring the stray contaminants that routinely cause false alarms in conventional aerosol detectors. In particular, the apparatus and method for detecting aerosol of the present invention capture an image of a light beam when aerosol is present, such that random contaminants that adhere to the walls of a detection chamber or that pass through the light beam do not affect the aerosol detection. Thus, the apparatus and method for detecting aerosol of the present invention more accurately detect aerosols than conventional aerosol detectors, which saves a significant amount of money that previously was expended in dealing with false alarms.

The apparatus for detecting aerosol of the present invention includes a light source for producing a light beam and at least one image sensor directed toward one or more respective portions of the light beam to capture at least one image of the light beam. Correspondingly, the method for detecting aerosol of the present invention includes transmitting a light beam, focusing at least one image sensor on a portion of the light beam, capturing an image of the light beam by the image sensor(s), and detecting aerosol if the image of the light beam has a predefined shape and at least a predetermined intensity. The image sensor therefore has a field of view that encompasses at least a portion of the light beam such that the image sensor detects an aerosol if the image has a predefined shape and at least a predetermined intensity. In embodiments of the apparatus of the present invention, the image sensor(s) may be directed toward a portion of the light beam in either a forward-scatter position or a back-scatter position relative to the light source, or may be positioned normal to the light beam.

In further embodiments of the apparatus and method of the present invention, at least a portion of the light beam may be transmitted through a housing. In embodiments of the apparatus that include such a housing, the housing defines an opening through which aerosol may enter the housing. Alternatively, the light source may produce a light beam having a wavelength that is not included in ambient light such that a housing is not necessary.

As different types of aerosol, such as aerosol having differently sized particles, respond differently to light of different wavelengths, the apparatus of one embodiment may include a light source capable of producing first and second light beams having first and second different wavelengths, respectively. Thus, the apparatus of this embodiment may be able to more reliably detect and distinguish between different types of aerosol.

In addition, some portion of the light beam of the apparatus and method may be incident upon a photodiode. The photodiode then may provide feedback regarding the intensity of the light beam, such as to a controller that may correspondingly drive the light source based on the feedback so that the intensity is maintained at a predetermined level. An alarm also may be included in some embodiments of the apparatus and method of the present invention. The alarm therefore may activate when the image sensor detects aerosol. In one embodiment, a plurality of alarms indicative of different levels of aerosol are provided.

In one embodiment, the image sensor repeatedly captures images of a portion of the light beam. In this embodiment, the image sensor detects the presence of aerosol if a predetermined number of images have the predefined shape and at least the predetermined intensity. As such, the apparatus of this embodiment avoids false alarms otherwise generated by a single spurious image. The apparatus may also include a plurality of image sensors directed to respective portions of the light beam. As such, aerosol may be detected if at least a predefined number of the image sensors capture images having the predefined shape and at least a predetermined intensity. As noted above, the plurality of image sensors may repeatedly capture images of respective portions of the light beam such that aerosol will be detected if a predefined number of images captured by at least the predefined number of image sensors have the predefined shape and at least the predetermined intensity. As such, the apparatus of this embodiment further reduces the likelihood of false alarms by requiring the repeated concurrence of a plurality of image sensors. Alternatively, the apparatus may include a plurality of light sources with the image sensor capable of capturing an image encompassing at least a portion of the light beams produced by the plurality of light sources, thereby broadening the region being monitored.

Further, the image sensor of one embodiment generates an image of a portion of the light beam that is comprised of a plurality of scan lines. As such, the image sensor can detect aerosol when the intensity of a portion of at least one scan line exceeds a predetermined threshold. More commonly, the image sensor detects aerosol when at least a predefined number of the scan lines include at least a portion that exceeds the predetermined threshold. As such, the apparatus of this embodiment also reliably detects aerosol while reducing the incidence of false alarms.

The apparatus and method are also capable of performing a built-in-test, such as to determine if dirt is building up on the lens of the image sensor of if the system is otherwise degrading. In this regard, the image sensor can capture images at different times. The apparatus can also include a controller for comparing the images to determine if the images are degrading over time. Additionally, or alternatively, the image sensor may capture an image of light reflected from a reference object having a predefined reflectivity. The controller of this embodiment can then analyze the image of light reflected from the reference object to detect system degradation.

The apparatus and method can also control system performance over time, such as to insure consistent performance even as the temperature fluctuates and the components age. In this regard, the apparatus may include a controller for controlling the intensity of the light beam produced by the light source and/or the gain associated with the image sensor. Additionally, or alternatively, the apparatus may include a thermal management system in thermal communication with the light source and/or the image sensor, such as to maintain the temperature of these components at a constant level.

Therefore, the apparatus and method of the present invention provide for the detection of aerosol when an image of the light beam has a predefined shape and at least a predetermined intensity, which greatly reduces the likelihood of false alarms due to stray contaminants because the stray contaminants do not cause the light beam to have the predefined shape or to meet the predetermined intensity.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
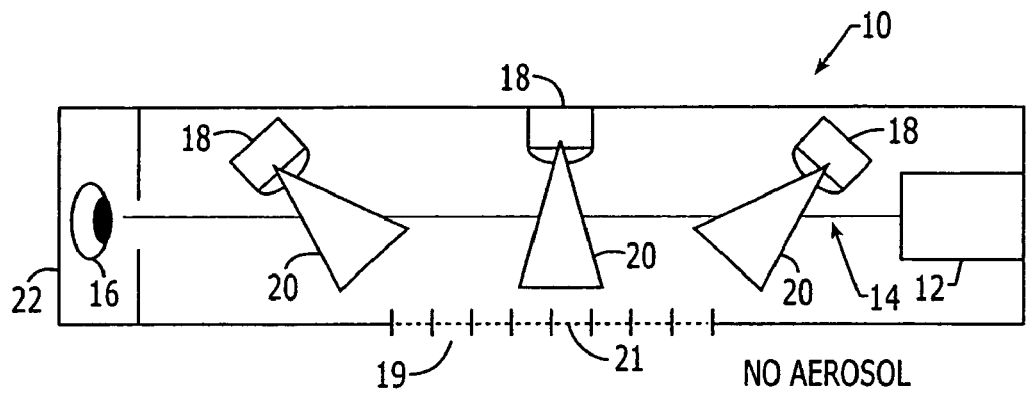
FIG. 1 illustrates a schematic view of an aerosol detector according to one embodiment of the present invention when aerosol is not present.

FIG. 1 illustrates one embodiment of the apparatus 10 for detecting aerosol of the present invention. The apparatus 10 includes one or more light sources 12 that produce respective light beams 14. The light source may be any type of light source capable of producing any type or wavelength of light beam that is known to those skilled in the art. In some embodiments of the apparatus of the present invention, the light source may include a light emitting diode (LED), incandescent lamp or a laser source. In addition, the light source may be chosen to produce a certain type of light beam. For instance, in various embodiments of the apparatus, the light source may produce a halogen light beam, a laser beam or any other type of collimated light beam. The light source(s) 12 may also be capable of producing first and second light beams having first and second wavelengths, respectively. The first and second wavelengths are different since light of different wavelengths may interact differently with different types of aerosol with different particle sizes such that additional information about the aerosol can be gathered.

In some embodiments of the apparatus 10, the light beam 14 may be incident upon a photodiode 16. The photodiode 16 may be any type of photodiode known to those skilled in the art. To prevent light other than the light beam 14 from contacting the photodiode 16, the photodiode may be located behind a barrier. The barrier defines an aperture through which the light beam 14 may be transmitted to be incident upon the photodiode, as indicated by the two partial lines between the photodiode 16 and the nearest image sensor 18 in FIGS. 1 and 2. While the photodiode 16 may be directly within the light beam 14 as shown, the photodiode may be offset from the light beam so as to receive scattered light in other embodiments. The photodiode 16 is capable of providing feedback to the light source 12 regarding at least the intensity of the light beam 14 such that the light source 12 may be adjusted appropriately to produce the desired intensity of the light beam 14. In other embodiments, a controller that is in communication with the light source 12 may receive the feedback from the photodiode 16, then communicate the appropriate adjustments to the light source 12, thereby driving the light source to produce the desired intensity of the light beam 14. The photodiode 16 also provides the necessary feedback regarding the light beam 14 for any type of test or check to ensure that the aerosol detector is functioning properly. For example, in the aircraft industry, a built-in-test (BIT) is typically performed periodically or prior to each flight to ensure that the light source is functioning properly. In addition, a reflective element or other reference object having a predefined reflectivity may be placed in a portion of the light beam 14 that is not used for aerosol detection to reflect light onto the image sensor 18 to verify that the image sensor is functioning properly. Still further, the image sensor 18 may capture a plurality of images at different times and the controller may compare the images from different times to detect any system degradation, such as due to a build-up of dust or dirt on the lens of the image sensor.

The apparatus 10 for detecting aerosol also includes at least one image sensor 18 directed toward a portion of the light beam 14 to capture an image of the light beam 14. As such, the field of view 20 of the image sensor(s) 18 may be larger than that portion of the light beam 14 captured by the image sensor(s), but, in any event, is sized to encompass at least a portion of the light beam. The image sensor(s) 18 may be any type of device capable of capturing an image of the light beam 14 known to those skilled in the art. In various embodiments of the apparatus 10, the image sensor may include an infrared-sensitive camera, a line scanning linear array or a video camera. For example, in an advantageous embodiment of the apparatus 10, the image sensor 18 includes a low light, black and white camera, model number PC 164C-EX commercially available from Supercircuits, Inc. for capturing images of the light beam 14.

Figure 2:
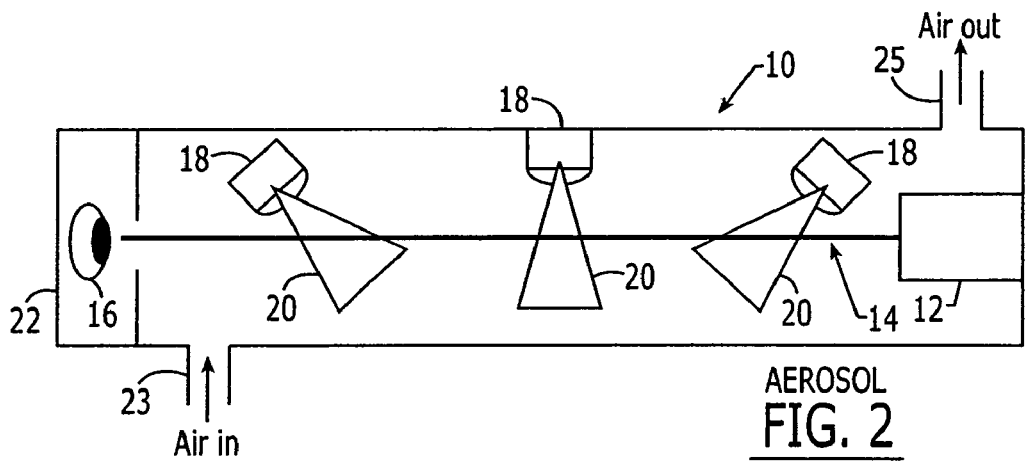
FIG. 2 illustrates a schematic view of an aerosol detector according to one embodiment of the present invention when aerosol is present.

In embodiments in which only one image sensor 18 is utilized, it may be positioned in a forward-scatter position relative to the light source 12. In FIGS. 1 and 2, the image sensor 18 that is closest to the photodiode 16 is positioned in a forward-scatter position relative to the light source 12. The forward-scatter position permits the image sensor 18 to view the light beam 14 from an angle at which the light beam 14 may look the brightest. The image sensors 18 may additionally or alternatively be positioned in a backscatter position relative to the light source 12 and/or a position normal to the light beam 14. Thus, in the embodiments illustrated in FIGS. 1 and 2, the image sensor that is closest to the light source 12 is positioned in a backscatter position, while the middle image sensor 18 is positioned normal to the light beam 14. In other embodiments the image sensor(s) may be positioned at a normal scatter angle or in any other manner or at any other angle as known to those skilled in the art. In addition, when more than one image sensor 18 is utilized, the field of view 20 of each image sensor 18 may be directed toward different portions of the light beam 14, as shown in the embodiments of FIGS. 1 and 2. Alternatively, the field of view of each image sensor 18 may be directed toward the same portion of the light beam 14. Still further, while the apparatus of the illustrated embodiment includes a single light source 12, the apparatus could include multiple light sources for producing respective light beams. In this embodiment, the image sensor may capture an image encompassing at least a portion of the light beams produced by each light source. Although not shown, the apparatus may include a light trap associated with each image sensor and positioned opposite the image sensor relative to the beam of light. The light trap prevents light from scattering behind the light beam and being collected by the image sensor.

The apparatus 10 for detecting aerosol may also include a housing 22 through which at least a portion of the light beam 14 extends. The image sensor(s) 18 may be located within the housing 22 or the image sensor(s) may be external to the housing, but may view the interior of the housing through a port or other opening. The light source 12 may also be located within the housing 22, as shown in the embodiments of FIGS. 1 and 2. Alternatively, the light source 12 may be located at least partially outside of the housing 22 and transmit the light beam 14 into the housing 22, such as through an opening defined by the housing 22. Typically, the housing 22 completely encloses the image sensor(s) 18 and at least a portion of the light beam 14, as shown in FIGS. 1 and 2, except for one or more openings defined by the housing through which aerosol may enter the housing. For example, as shown in the embodiment of FIG. 1, the housing 22 may define one or more openings 19 through which air may enter and exit the housing. The opening(s) 19 may be any type of aperture in the housing 22, such as holes and/or slots of any size. In one embodiment of the housing 22, the opening(s) 19 may be covered with a mesh material 21, such as a mesh with openings of ¹⁄₃₂-inch, to prevent contaminants from entering the housing through the opening(s) 19. In other embodiments, the opening(s) 19 may include one or more bent or curved elements, such as a labyrinth structure, that prevent light from outside the housing 22 from entering the housing, such as light stop elements. Another example of the type of opening (s) that may be defined in the housing 22 is illustrated in the embodiment of FIG. 2. In this embodiment, the housing 22 may define at least one air inlet 23 and at least one air outlet 25 to permit air to flow through the housing 22. If more than one air inlet is utilized, then air may be sampled from more than one location, then drawn to a central detector, such as via a duct or a network of ducts. The inlet(s) and outlet(s) may be configured in any manner known to those skilled in the art, such as in conventional aspirated detectors.

The housing 22 may be made of any type material that provides sufficient rigidity to support the image sensor(s) 18 and to provide a chamber within which aerosol detection may occur. For example, the housing 22 may be made of plastic, metal, or any other appropriate material. In addition, the interior of the housing may be coated with a non-reflective or flat black coating.

The housing 22 is generally designed to permit aerosol detection without exposure to ambient light. In one embodiment, the light source 12 may produce a light beam 14 having a wavelength that is not present in the ambient light. In this embodiment, a housing need not be employed since the ambient light will not adversely impact aerosol detection.

Figure 3:
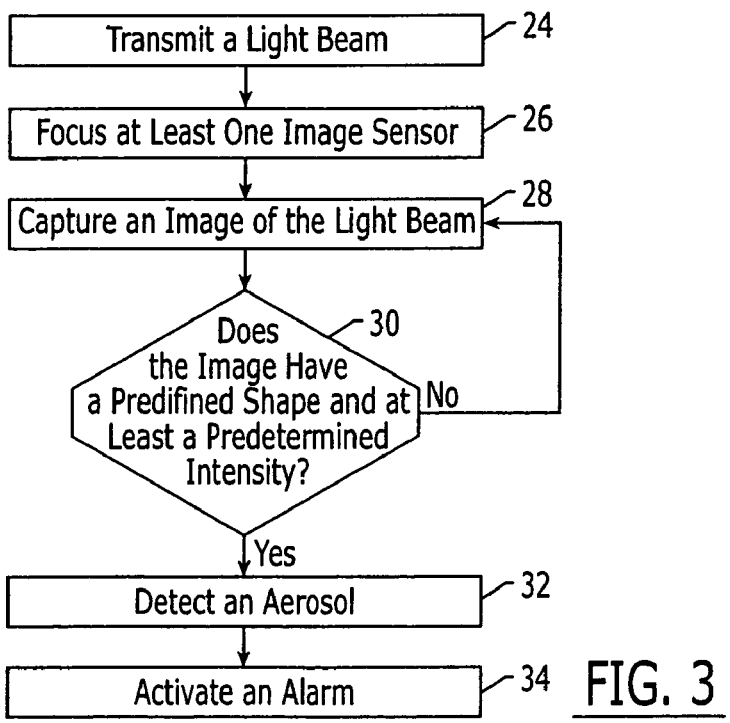
FIG. 3 is a flow diagram of the method of aerosol detection according to one embodiment of the present invention.

The apparatus operates continuously or periodically with repeated passes through the flow diagram of FIG. 3, which illustrates one embodiment of a method for detecting aerosol. In this embodiment, a light beam 14 is transmitted (block 24), such as through a housing 22 and/or to a photodiode 16, as described above. At least one image sensor 18 is then focused on at least one portion of the light beam 14 (block 26). In certain embodiments, the image sensor(s) 18 may have a field of view that is larger than the portion of the light beam 14 upon which the image sensor(s) are focused, as further explained above. To reduce false alarms, the image sensor may be masked or may look through an aperture, or the image captured by an image sensor may be processed so that the image sensor only views the light beam. An image of the light beam 14 is captured by the image sensor(s) 18 (block 28). In some embodiments, a continuous or periodic sequence of images of the light beam 14 may be captured by the image sensor(s) 18.

The images of the light beam 14 that are captured by the image sensor(s) 18, are then analyzed to determine whether the image has a predefined shape and at least a predetermined intensity (block 30). The analysis may be carried out by any type of device known to those skilled in the art that is capable of comparing the captured images to stored information regarding a shape and intensity of a light beam when an aerosol is present. For example, the image sensor(s) 18 may be in communication with a controller or other processing element that performs such analysis, such as via wireline or wireless communication and/or via a local or wide area network. In other embodiments, the processing element may be a part of the image sensor(s) 18. In addition, a graphics analyzer may be utilized to detect the shape of the portion of the image of the light beam 14 that is captured by the image sensor(s) 18. An intensity detector is also utilized to measure the intensity of the portion of the image of the light beam 14 that is capture by the image sensor(s) 18. The graphics analyzer and/or the intensity detector may be embodied in one or more separate modules that are in communication with the processing element or the graphics analyzer and/or the intensity detector may be part of the processing element.

Figure 4:
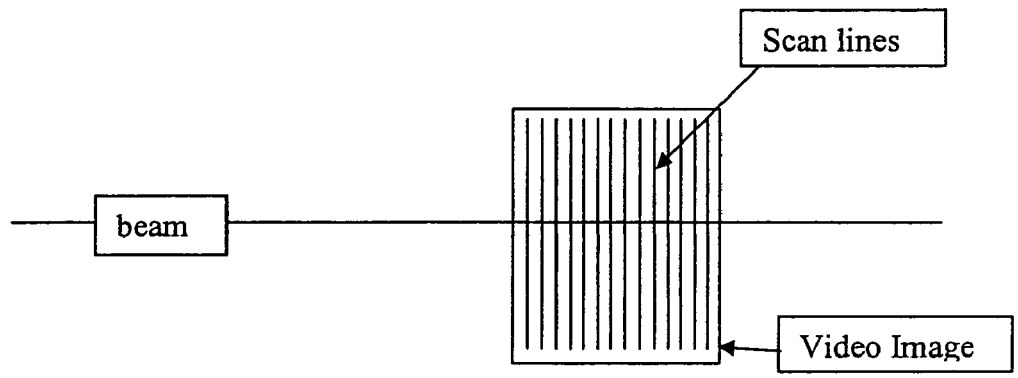
FIG. 4 illustrates a schematic view of an image of a light beam when aerosol is present.
Figure 5:
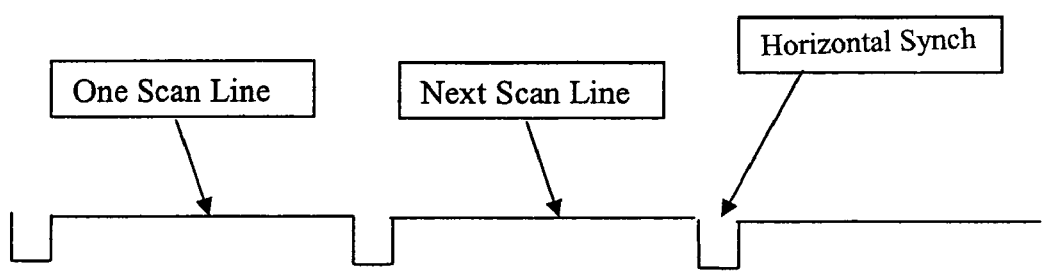
FIG. 5 illustrates a series of scan lines separated by a horizontal synchronization signal.
Figure 6:
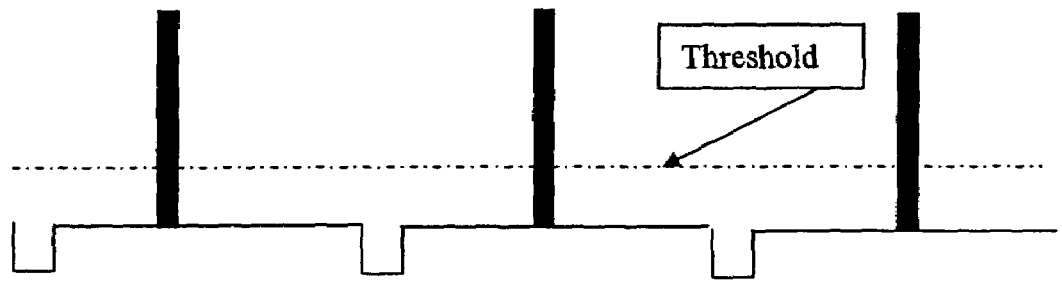
FIG. 6 illustrates the series of scan lines as in FIG. 5, but with spikes shown as darkened vertical lines which are indicative of the presence of an aerosol.

In one embodiment of the present invention, the image sensor 18, such as a line scanning linear array, may repeatedly scan a portion of the light beam to generate an image or frame comprised of a plurality of scan lines as shown schematically in FIG. 4. As shown, scan lines are generally oriented normal to the direction of propagation of the light beam. The image sensor of this embodiment advantageously repeatedly captures images of the light beams, such as approximately thirty times a second. As shown schematically in FIG. 5, each scan line in an image is linked to adjacent scan lines by an identifying signal, such as a horizontal synchronization signal. When an aerosol is present, at least a portion of the image has greater intensity as represented schematically by spikes shown as darkened vertical lines in the scan lines of FIG. 6.

In order to detect the presence of aerosol, the threshold is defined to be somewhat greater than the intensity of a scan line in the absence of aerosol, but to be less than the intensity of a scan line in instances in which aerosol of a predetermined concentration is present. As such, aerosol can be detected if a portion of a scan line exceeds the threshold. In order to reduce the incidence of false alarms, the image sensor may detect aerosol in instances in which portions of a predefined number of adjacent scan lines all exceed the threshold. Moreover, in embodiments in which the image sensor generates a series of images, each comprised of a plurality of scan lines, the image sensor may require portions of the scan lines from each of a predefined number of images to exceed the threshold before identifying the presence of aerosol in order to further avoid false alarms due to spurious signals in a single image. Further, the predefined number of images may be required to be consecutive or may be required to be identified within a predetermined number of images, such as in 7 of 10 consecutive images. By monitoring the output of the light source 12 with a photodiode 16, the threshold can be adjusted upwardly or downwardly as the intensity of the light emitted by the light source similarly varies upwardly or downwardly, respectively. Any other technique for analyzing the images, such as any other analog or digital analysis of the image, also or alternatively may be utilized.

Figure 7:
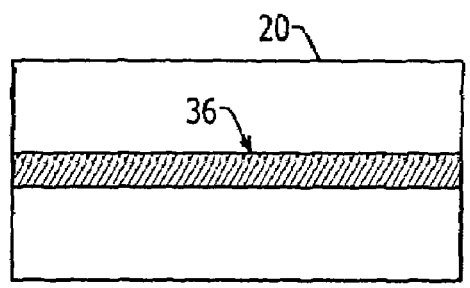
FIG. 7 illustrates the illuminated rectangular band that may be created by scattering from the aerosol particles.

Thus, in one embodiment, when an aerosol is present, the aerosol particles scatter the light of the light beam 14 and the light beam 14 appears as an illuminated rectangular band 36, as shown in FIG. 7, where the light beam 14 intersects with the field of view 20 of the image sensor(s) 18. In addition, as shown in the embodiments illustrated in FIGS. 1 and 2, the light beam 14 is illustrated as a darker line in FIG. 2 when aerosol is present than in FIG. 1 when no aerosol is present, to indicate that at least a portion of the light beam has a different size and intensity when aerosol is present than when aerosol is not present. As known to those skilled in the art, Raleigh and Mie scattering theories describe how light is scattered from aerosols depending upon the relative size of the aerosol particles to the light wavelength. In addition, the intensity of the light beam 14 is a function of the concentration and refractive properties of the aerosol particles. As such, when it is determined that at least one image of light beam 14 has a predefined shape, such as the rectangular band shape described above, and a predetermined intensity, then aerosol has been detected (block 32). If the image of the light beam 14 does not have the predefined shape or the predetermined intensity, then aerosol has not been detected and the process continues with the capturing of another image of the light beam (block 28). In embodiments in which multiple image sensors 18 are focused on different portions of the light beam 14, the multiple resulting images from the different image sensors may all be analyzed to determine if at least one of them has the predefined shape and at least the predetermined intensity that would indicate that aerosol is present. In other embodiments, more than one of the images from different portions of the light beam 14 as captured by the various image sensors, such as a predefined number of images, may have to have the predefined shape and at least the predetermined intensity before there is an indication that aerosol is present by the processing element. Further, other embodiments of the present invention may require not only a predefined number of image sensors to generate an image having the predefined shape and at least the determined intensity, but also require each of these image sensors to capture a predefined number of images having the predefined shape and at least the predetermined intensity.

If aerosol is detected, then an alarm may be activated (block 34). The alarm may be any type of alarm known to those skilled in the art. For example, the alarm may create a noise and/or illuminate a light when aerosol is detected. The alarm also may or alternatively may provide a signal, such as an analog or digital signal, to a controller that initiates an alarm or any other type of activity known to those skilled in the art to occur. The alarm may be a separate device that is in communication with the processing element described above or the alarm may be part of the processing element. As such, in the embodiments of the present invention in which the processing element is part of the image sensor(s) 18, the alarm may also be part of the image sensor(s) or a separate component. Further, the apparatus 10 may include a plurality of alarms, each indicative of different levels of aerosol.

In further embodiments, the sequence of images may be compared to detect any change in the amount of aerosol. Thus, the captured images may be utilized to determine if aerosol concentrations are increasing or decreasing. In addition, the captured images may be utilized to identify trends and/or perform statistical analysis that may be utilized to reduce false alarms.

The apparatus 10 and method can also control system performance over time, such as to insure consistent performance even as the temperature fluctuates and the components age. In this regard, the apparatus 10 may include a controller for controlling the intensity of the light beam produced by the light source 12 and/or the gain associated with the image sensor 18. Additionally, or alternatively, the apparatus 10 may include a thermal management system, such as a thermoelectric cooler, a heat sink or the like, in thermal communication with the light source 12 and/or the image sensor 18, such as to maintain the temperature of these components at a constant level.

The apparatus 10 and method for detecting aerosol of the present invention is particularly advantageous because it detects aerosols only if the image of the light beam 14 has a predefined shape and a predetermined intensity. Therefore, the risk of false alarms based upon the scattering of light by stray contaminants that interfere with the light beam or that adhere to the walls of the housing is not a concern when utilizing the apparatus and method of the present invention. Because the apparatus and method of the present invention will not detect a light beam having a predefined shape and a predetermined intensity when the stray contaminants interfere with the light beam or adhere to the walls of the housing, the apparatus and method of the present invention will not detect aerosol in those cases and, therefore, will not activate any alarm.

The apparatus and method for detecting aerosol of the present invention, therefore, permit the accurate detection of aerosol, including smoke, while ignoring the stray contaminants that routinely cause false alarms in conventional aerosol detectors. In particular, the apparatus and method for detecting aerosol of the present invention sense an image of a light beam when aerosol is present, such that random contaminants that adhere to the walls of a detection chamber or that pass through the light beam do not affect the aerosol detection. Thus, the apparatus and method for detecting aerosol of the present invention more accurately detect aerosols than conventional aerosol detectors, which saves a significant amount of money that previously was expended in dealing with false alarms.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for detecting aerosol, comprising:
a light source for producing a light beam; and
an image sensor having a field of view and directed toward a portion of the light beam to capture an image thereof, wherein said image sensor detects aerosol if the image has a predefined rectangular band shape that is illuminated within the larger field of view and also if the image has at least a predetermined intensity, and
wherein said image sensor fails to detect aerosol if the image has no predefined rectangular band shape that is illuminated within the larger field of view even though the light source continues to produce the light beam and the image sensor continues to capture an image of the field of view.

2. The apparatus of claim 1, wherein said image sensor is directed toward a portion of the light beam in a forward-scatter position relative to said light source.

3. The apparatus of claim 1, wherein said image sensor is directed toward a portion of the light beam in a reverse-scatter position relative to said light source.

4. The apparatus of claim 1, wherein said image sensor repeatedly captures images of the portion of the light beam, and wherein said image sensor detects aerosol if a predefined number of images have the predefined shape and at least the predetermined intensity.

5. The apparatus of claim 1, wherein said image sensor comprises a plurality of image sensors directed toward respective portions of said light beam.

6. The apparatus of claim 5, wherein aerosol is detected if at least a predefined number of the image sensors capture images having the predefined shape and at least the predetermined intensity.

7. The apparatus of claim 5, wherein the plurality of image sensors repeatedly capture images of respective portions of the light beam, and wherein aerosol is detected if a predefined number of images captured by at least a predefined number of the image sensors have the predefined shape and at least the predetermined intensity.

8. The apparatus of claim 1, further comprising a photodiode for providing feedback regarding an intensity of the light beam.

9. The apparatus of claim 8, further comprising a controller for driving said light source based upon the feedback provided by said photodiode such that the intensity of the light beam is maintained at a predetermined level.

10. An apparatus for detecting aerosol, comprising:
a light source for producing a light beam; and
an image sensor directed toward a portion of the light beam to capture an image thereof, wherein said image sensor generates an image of a portion of the light beam comprised of a plurality of scan lines,
wherein said image sensor detects aerosol when the image has a predefined shape and an intensity of a portion of at least one scan line exceeds a predetermined threshold.

11. The apparatus of claim 10, wherein said image sensor detects aerosol when at least a predefined number of the scan lines include at least a portion that exceeds the predetermined threshold.

12. The apparatus of claim 1, wherein said image sensor is capable of capturing a plurality of images at different times, and wherein the apparatus further comprises a controller for comparing the plurality of images to determine if the images are degrading.

13. The apparatus of claim 1, wherein said image sensor is capable of capturing an image of light reflected from a reference object having a predefined reflectivity, and wherein the apparatus further comprises a controller for analyzing the image of light reflected from the reference object.

14. A method for detecting aerosol, comprising:
transmitting a light beam;
focusing at least one image sensor having a field of view on at least one portion of the light beam;
capturing an image of the light beam by the at least one image sensor;
detecting aerosol if the image of the light beam has a predefined rectangular band shape that is illuminated within the larger field of view and also if the image has at least a predetermined intensity;
providing an alarm signal indicative of detection of aerosol; and failing to detect aerosol if the image has no predefined rectangular band shape that is illuminated within the larger field of view even though the light beam continues to be transmitted and the image sensor continues to capture the image of the light beam.

15. The method of claim 14, wherein transmitting a light beam comprises transmitting a light beam having a wavelength not otherwise included in ambient light.

16. The method of claim 14, wherein transmitting a light beam comprises transmitting the light beam such that some portion of the light beam is incident upon a photodiode; and further comprising providing feedback regarding an intensity of the light beam via the photodiode.

17. The method of claim 16, wherein driving said light source based upon the feedback provided by the photodiode such that the intensity of the light beam is maintained at a predetermined level.

18. The method of claim 14, wherein capturing an image comprises repeatedly capturing images of the light beam, and wherein detecting aerosol comprises detecting aerosol if a predefined number of images have the predefined shape and at least the predetermined intensity.

19. The method of claim 14, wherein capturing an image of the light beam comprises capturing images of respective portions of the light beam with a plurality of image sensors, and wherein detecting aerosol further comprises detecting aerosol if at least a predefined number of the image sensors capture images having the predefined shape and at least the predetermined intensity.

20. The method of claim 14, wherein capturing an image of the light beam comprises repeatedly capturing images of respective portions of the light beam with a plurality of image sensors, and wherein detecting aerosol comprises detecting aerosol if at least a predefined number of images captured by at least a predefined number of the image sensors have the predefined shape and at least the predetermined intensity.

21. A method for detecting aerosol, comprising:
transmitting a light beam;
focusing at least one image sensor on at least one portion of the light beam;
capturing an image of the light beam by the at least one image sensor, wherein capturing an image of the light beam comprises generating an image of a portion of the light beam comprised of a plurality of scan lines;
detecting aerosol if the image of the light beam has a predefined shape and at least a predetermined intensity, wherein detecting aerosol comprises detecting aerosol when an intensity of a portion of at least one scan line exceeds a predetermined threshold; and
providing an alarm signal indicative of detection of aerosol.

22. The method of claim 21, wherein detecting aerosol comprises detecting aerosol when at least a predefined number of the scan lines include at least a portion that exceeds the predetermined threshold.

23. The method of claim 14, wherein transmitting a light beam comprises transmitting a plurality of light beams, and wherein capturing an image of the light beam comprises capturing an image encompassing at least a portion of the plurality of light beams.

24. The method of claim 14, wherein capturing an image of the light beam comprises capturing a plurality of images at different times, and wherein the method further comprises comparing the plurality of images to determine if the images are degrading.

25. The method of claim 14, further comprises:
capturing an image of light reflected from a reference object having a predefined reflectivity; and
analyzing the image of light reflected from the reference object.

* * * * *